US012728154B2

(12) United States Patent
Kwon et al.

(10) Patent No.: US 12,728,154 B2
(45) Date of Patent: Sep. 8, 2026

(54) EXOSOMES COMPRISING CORONAVIRUS-DERIVED ANTIGEN PROTEIN OR GENE ENCODING SAME PROTEIN, AND USE OF SAME

(71) Applicants: EXOLLENCE CO., LTD., Seoul (KR); EWHA UNIVERSITY-INDUSTRY COLLABORATION FOUNDATION, Seoul (KR)

(72) Inventors: Ki Hwan Kwon, Seoul (KR); Ji Hwa Chung, Gimpo-si (KR)

(73) Assignees: EXOLLENCE CO., LTD., Seoul (KR); EWHA UNIVERSITY-INDUSTRY COLLABORATION FOUNDATION, Seoul (KR)

( * ) Notice: Subject to any disclaimer, the term of this patent is extended or adjusted under 35 U.S.C. 154(b) by 527 days.

(21) Appl. No.: 18/351,512

(22) PCT Filed: Jan. 14, 2022

(86) PCT No.: PCT/KR2022/000736
§ 371 (c)(1),
(2) Date: Jul. 13, 2023

(87) PCT Pub. No.: WO2022/154576
PCT Pub. Date: Jul. 21, 2022

(65) Prior Publication Data

US 2024/0316182 A1 Sep. 26, 2024

(30) Foreign Application Priority Data

Jan. 14, 2021 (KR) ........................ 10-2021-0005318

(51) Int. Cl.

| | |
|---|---|
| ***A61K 39/00*** | (2006.01) |
| ***A61K 9/19*** | (2006.01) |
| ***A61K 9/50*** | (2006.01) |
| ***A61K 39/215*** | (2006.01) |
| ***A61P 31/14*** | (2006.01) |
| ***C07K 14/165*** | (2006.01) |
| ***C12N 7/00*** | (2006.01) |

(52) U.S. Cl.
CPC ................ *A61K 39/00* (2013.01); *A61K 9/19* (2013.01); *A61K 9/5063* (2013.01); *A61K 39/215* (2013.01); *A61P 31/14* (2018.01); *C12N 7/00* (2013.01); *A61K 2039/55555* (2013.01); *A61K 2039/572* (2013.01); *C12N 2770/20033* (2013.01)

(58) Field of Classification Search
CPC .................. A61K 39/12; A61K 39/215; A61K 2039/55555; C12N 2770/20034; C07K 14/70596
See application file for complete search history.

(56) References Cited

FOREIGN PATENT DOCUMENTS

| | | | |
|---|---|---|---|
| KR | 10-2020-0053531 | | 5/2020 |
| WO | 2018/221954 | A1 | 12/2018 |
| WO | 2020-191361 | A2 | 9/2020 |
| WO | 2020-257720 | A1 | 12/2020 |

OTHER PUBLICATIONS

Thery et al., Membrane vesicles as conveyors of immune responses, National Reviews Immunology, Jun. 5, 2009, pp. 581-593, vol. 9, Macmillan Publishers Limited, United Kingdom.
Polak et al., Extracellular versicle-based vaccine platform displaying native viral envelope proteins elicits a robust anti-SARS-CoV-2 response in mice, Oct. 28, 2020, pp. 1-30, bioRxiv preprint, United States.
Tsai et al., Exosome-Mediated mRNADelivery for SARS-CoV-2 Vaccination, Nov. 6, 2020, pp. 1-49, bioRxiv preprint, United States.
Cheng et al. "Exomes from M1-Polarized Macrophages Potentiate the Cancer Vaccine by Creating a Pro-infammatory Microenvironment in the Lymph Node", Molecular Therapy, Jul. 2017, pp. 1665-1675, vol. 25, No. 7, American Society of Gene & Cell Therapy, USA.
Yamashita et al. "Possibility of Exosome-Based Therapeutics and Challenges in Production of Exosomes Eligible for Therapeutic Application", Biol. Pharm. Bull., 2018, pp. 835-842, vol. 41, No. 6, The Pharaceutical Society of Japan, Japan.

*Primary Examiner* — Barry A Chestnut
(74) *Attorney, Agent, or Firm* — AJU IP Global PLLC

(57) ABSTRACT

The present invention relates to an extracellular vesicle including a coronavirus-derived antigen protein or a gene encoding the protein, and a use of the extracellular vesicle. According to the present invention, when mice are immunized by administering an activated immune cell-derived extracellular vesicle loaded with an antigen protein or mRNA, excellent antigen-specific neutralizing antibody production and T cell response induction effects are confirmed. When the extracellular vesicle is stored under room-temperature and refrigerated conditions after freeze-drying, high stability and an excellent antibody production effect are experimentally confirmed. From these results, the extracellular vesicle according to the present invention or a vaccine composition including the same may serve as a platform applicable to various diseases with an excellent antigen-specific immune response induction effect and excellent stability, and thus is expected to be effectively used for the development of vaccines for preventing or treating various diseases including infectious diseases, particularly coronavirus infections.

12 Claims, 17 Drawing Sheets

[Figure 1A]
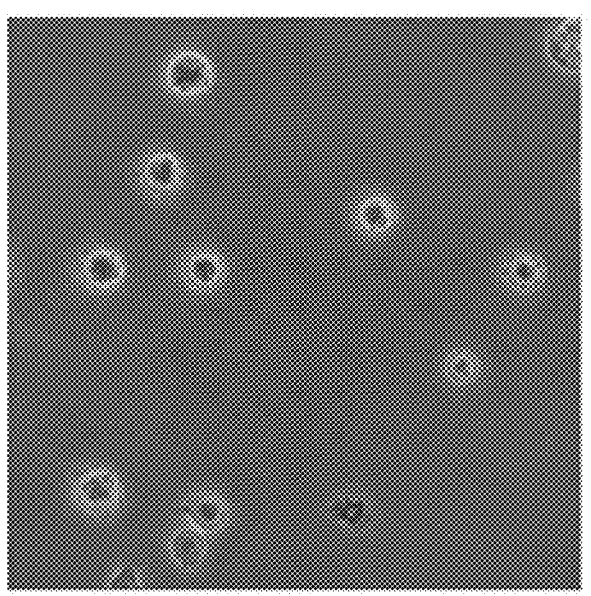
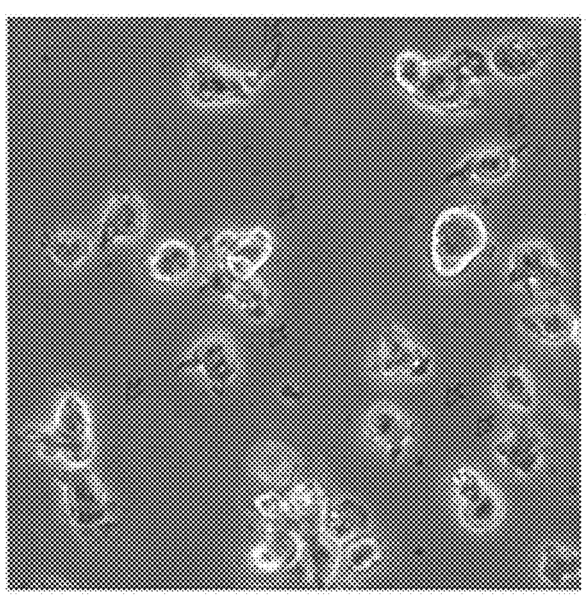

[Figure 1B]

[Figure 2A]
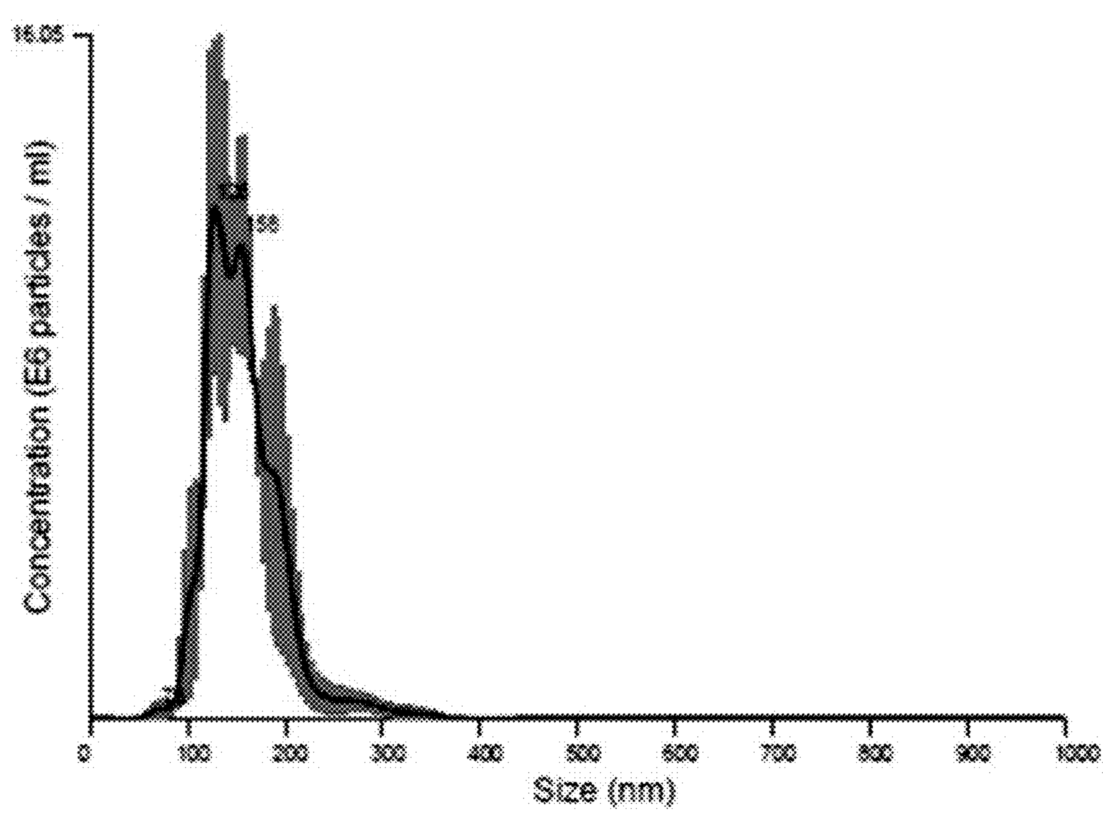

[Figure 2B]
Transmission electron microscope (TEM)
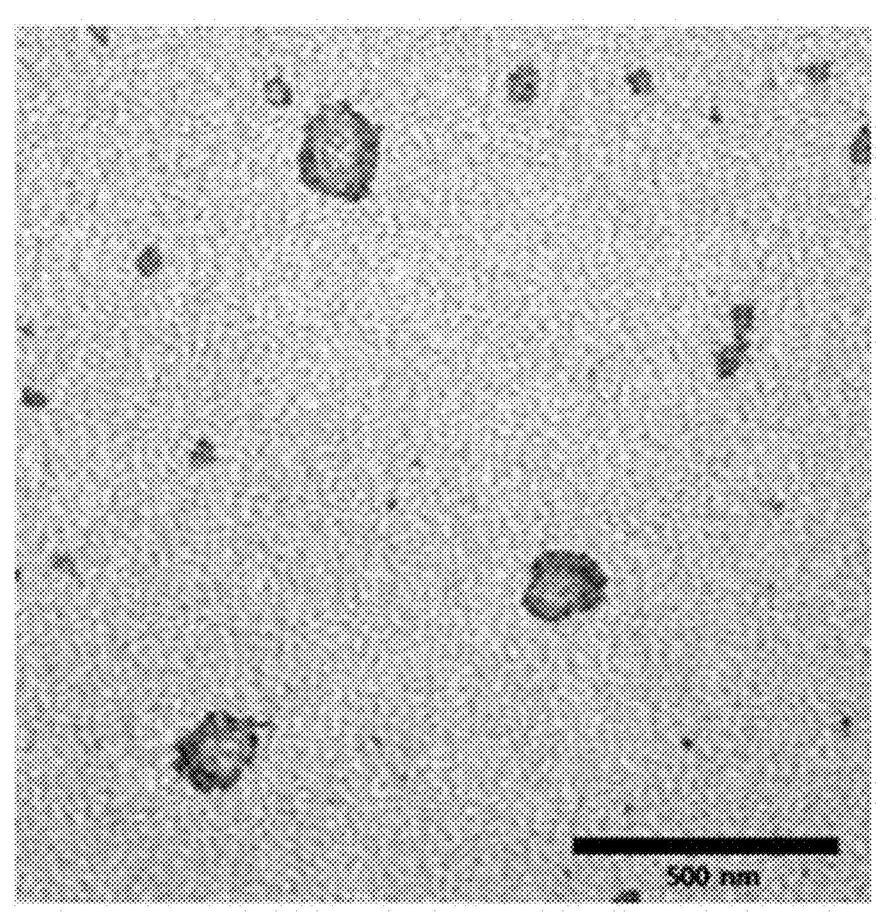

[Figure 2C]
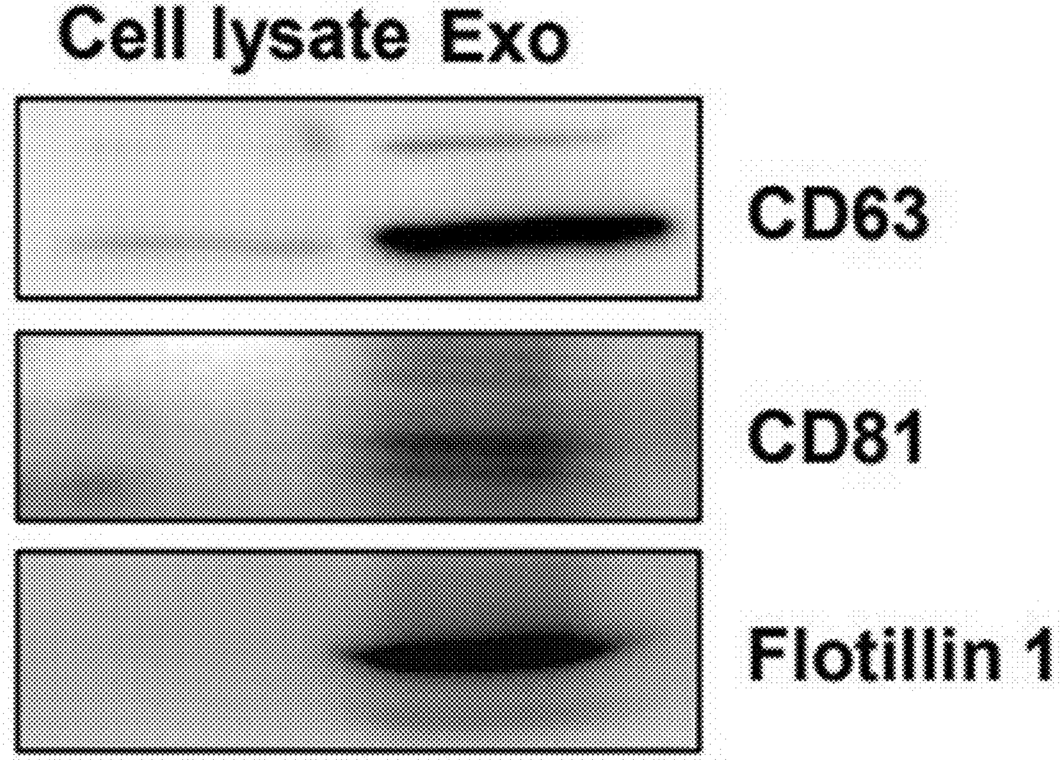

[Figure 3A]
*In vivo* immunization schedule
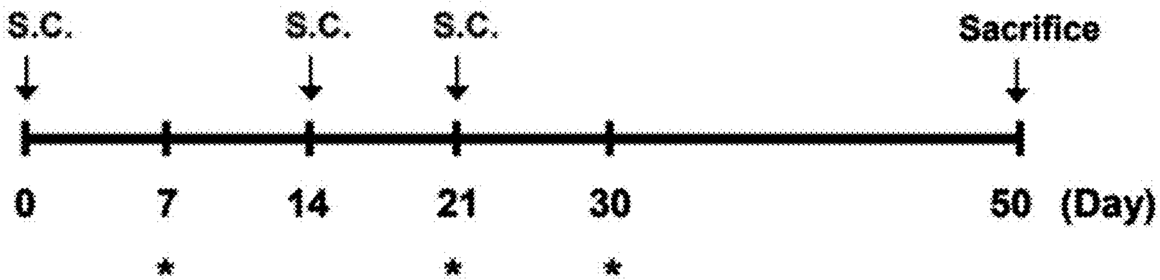
S.C. : subcutaneous injection with COVID 19-ImmunExo
* Blood collection and SARS-CoV 2 surrogate neutralization test

[Figure 3B]
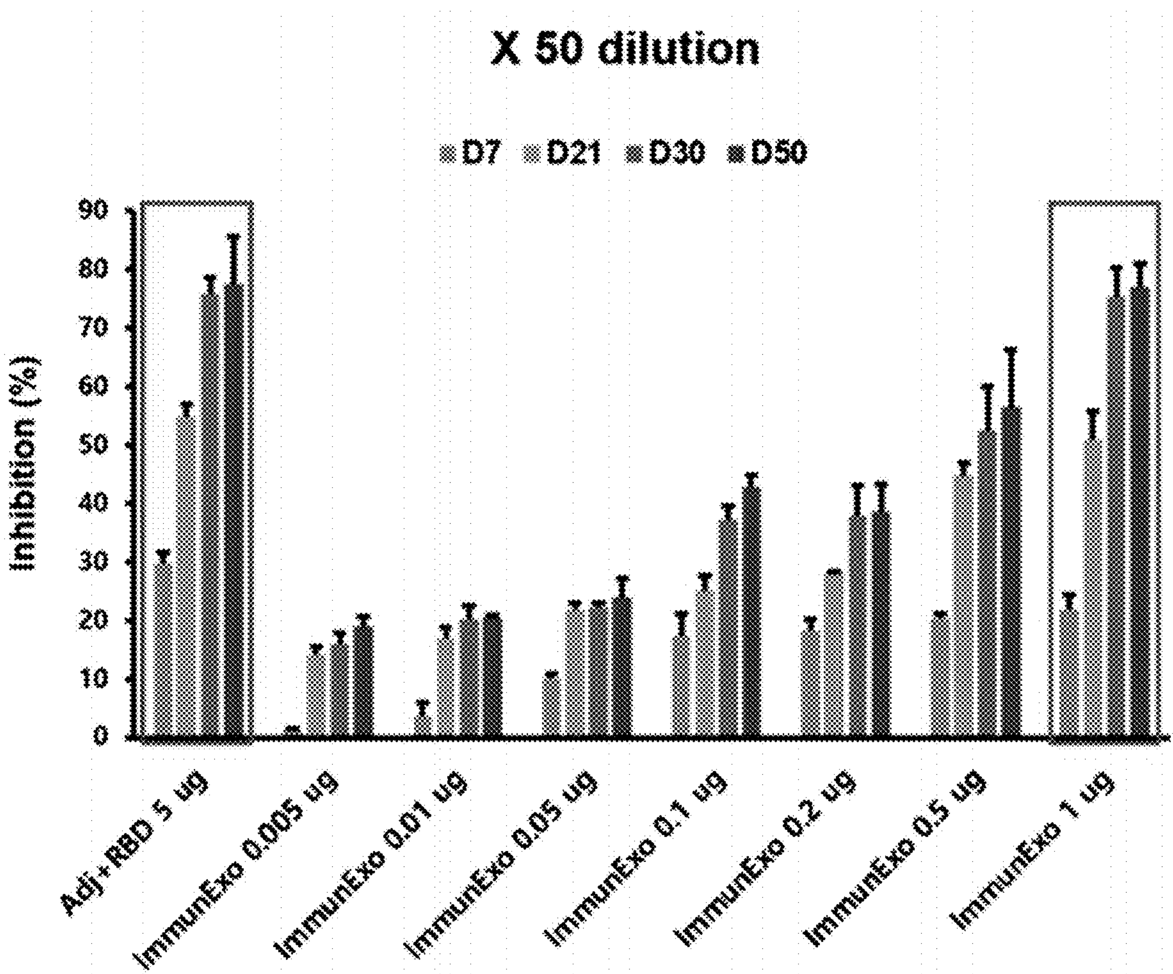

[Figure 3C]
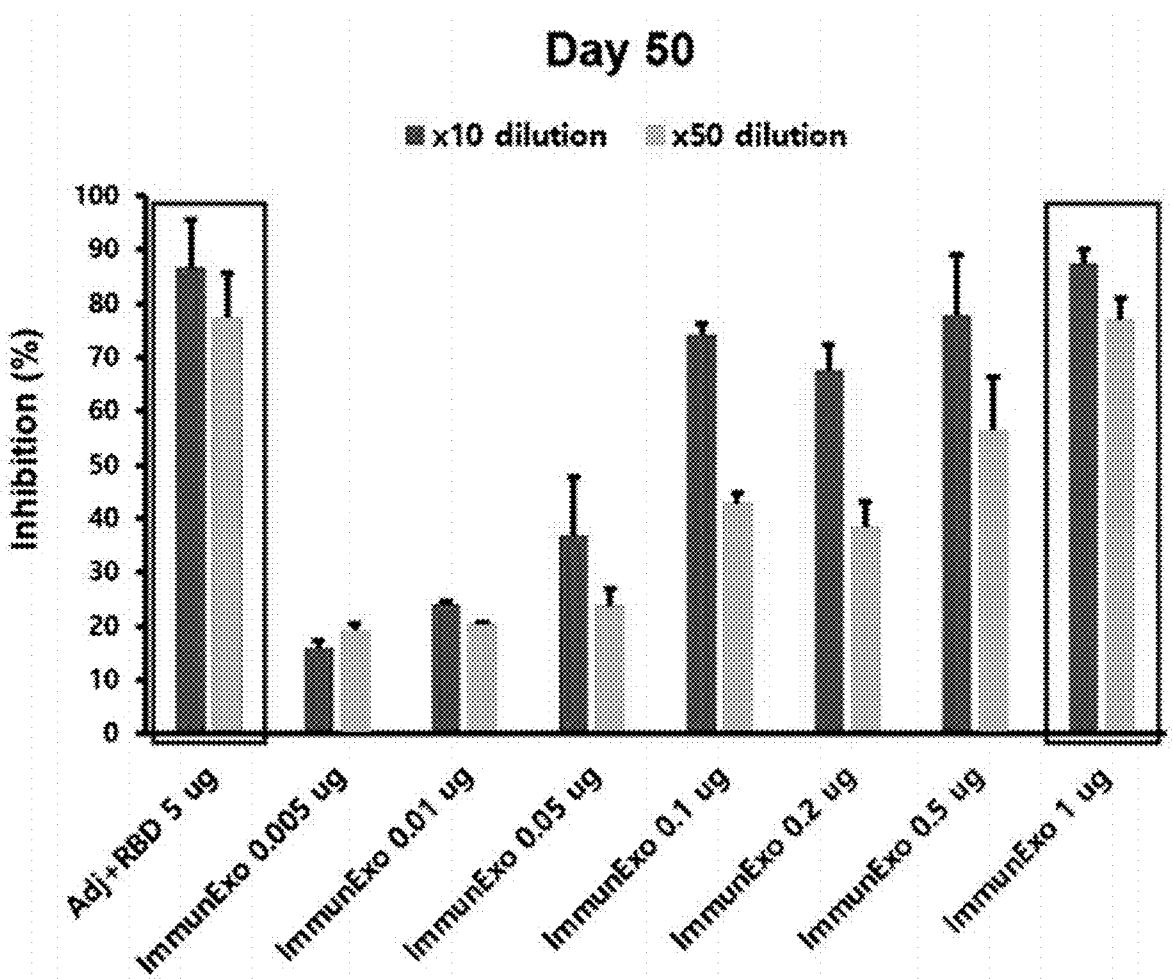

[Figure 4A]
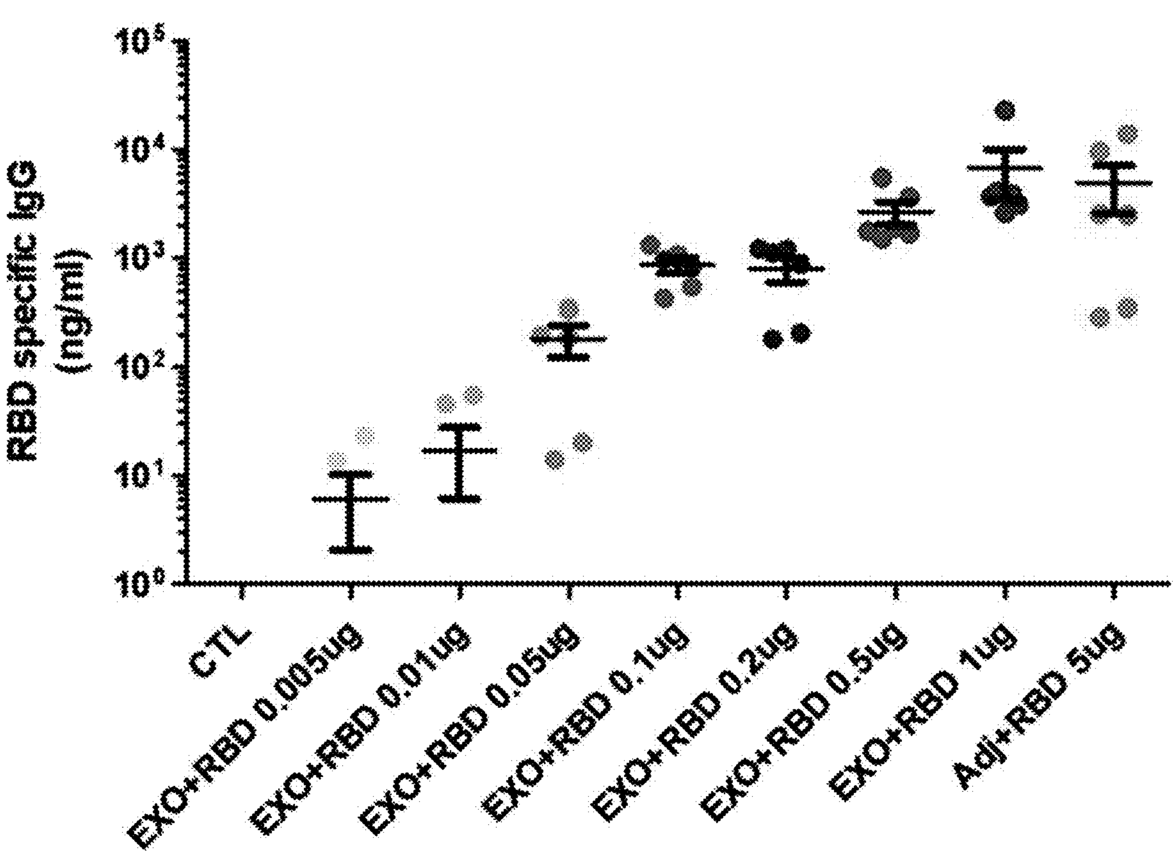

[Figure 4B]
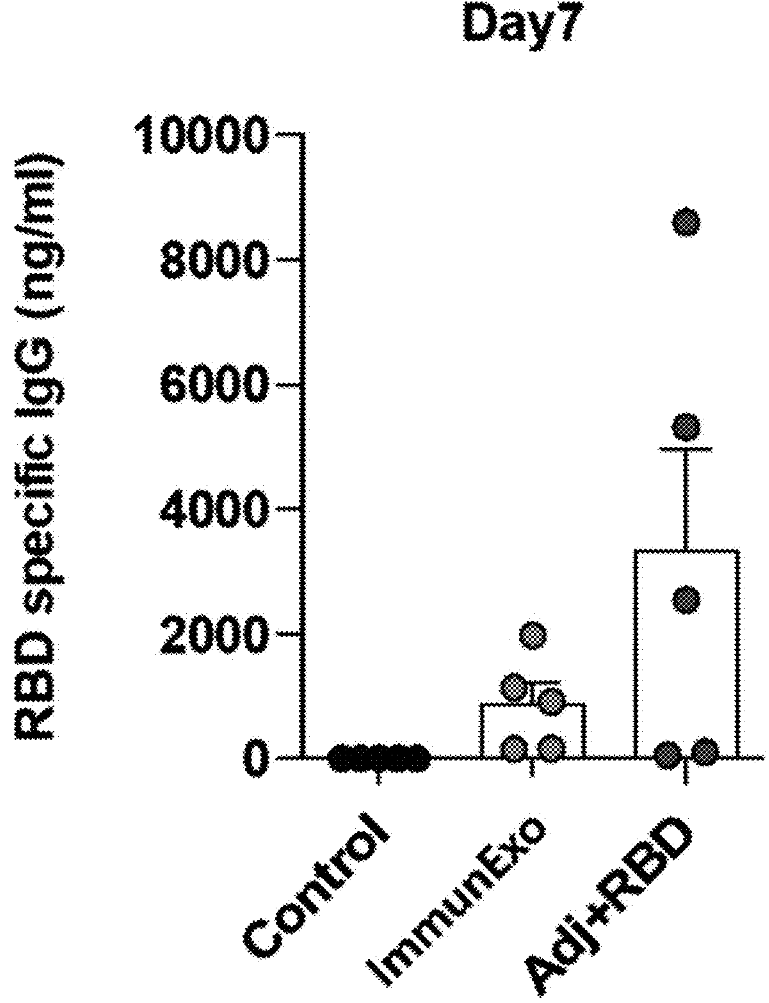

[Figure 4C]
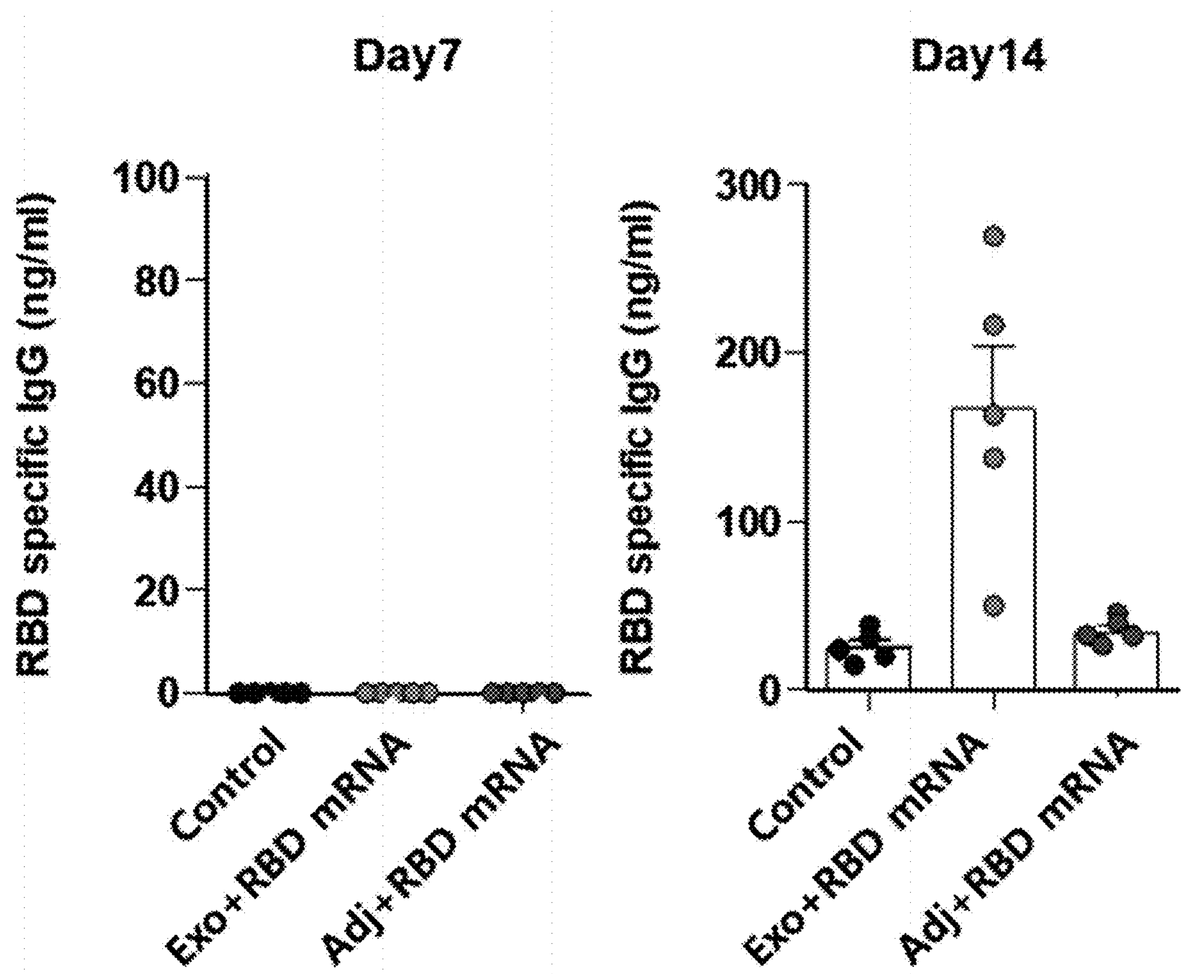

[Figure 4D]
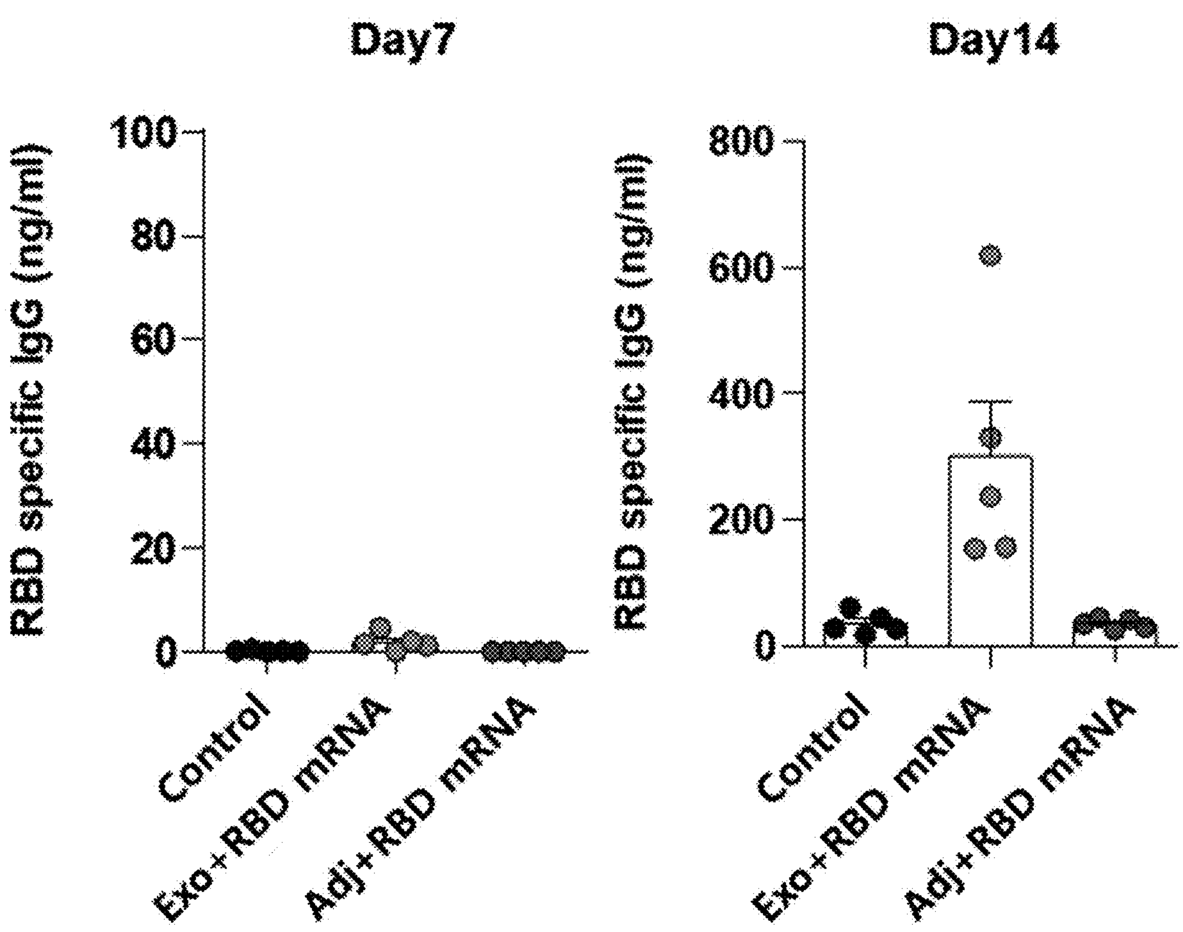

[Figure 5A]
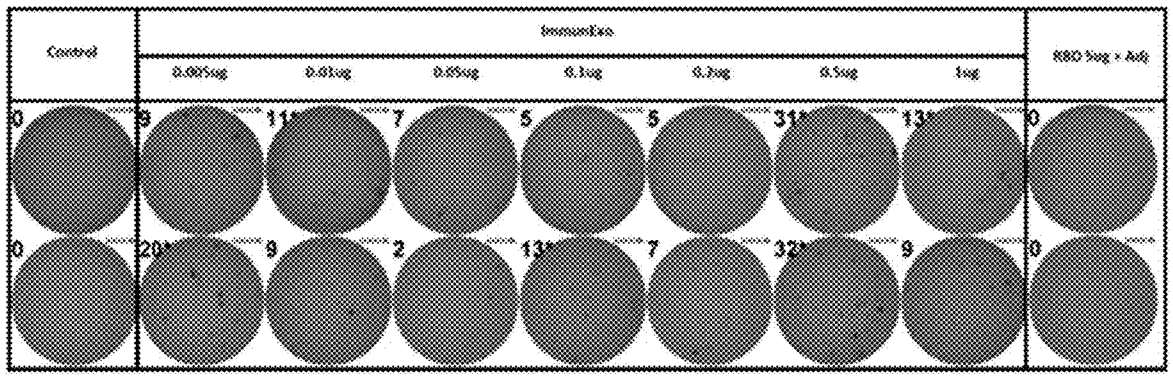
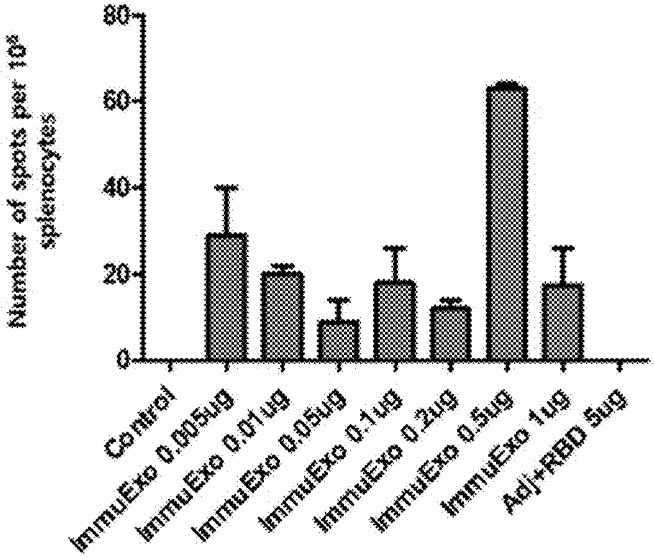

[Figure 5B]

[Figure 6A]
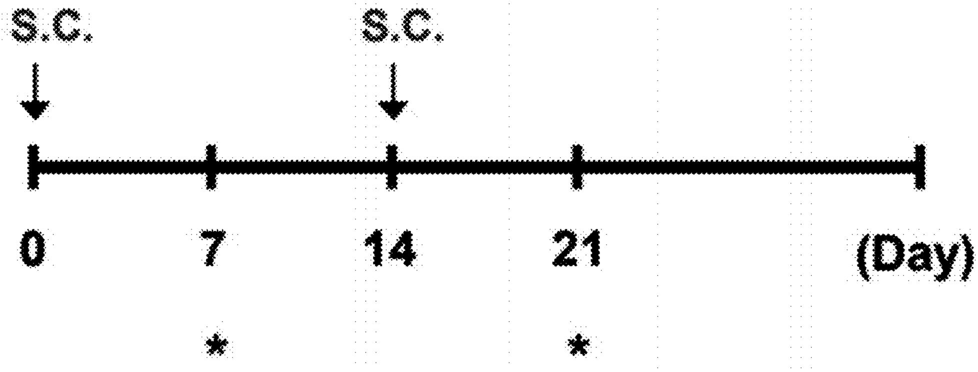

[Figure 6B]
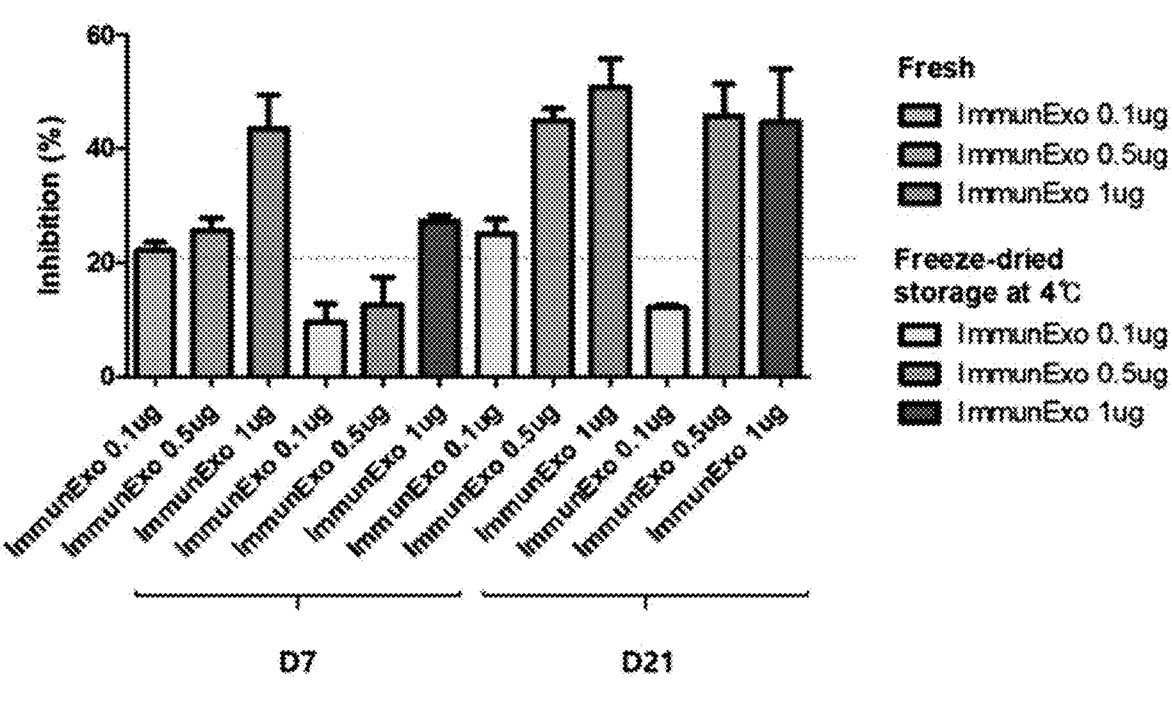
* Cut off 20%

[Figure 6C]
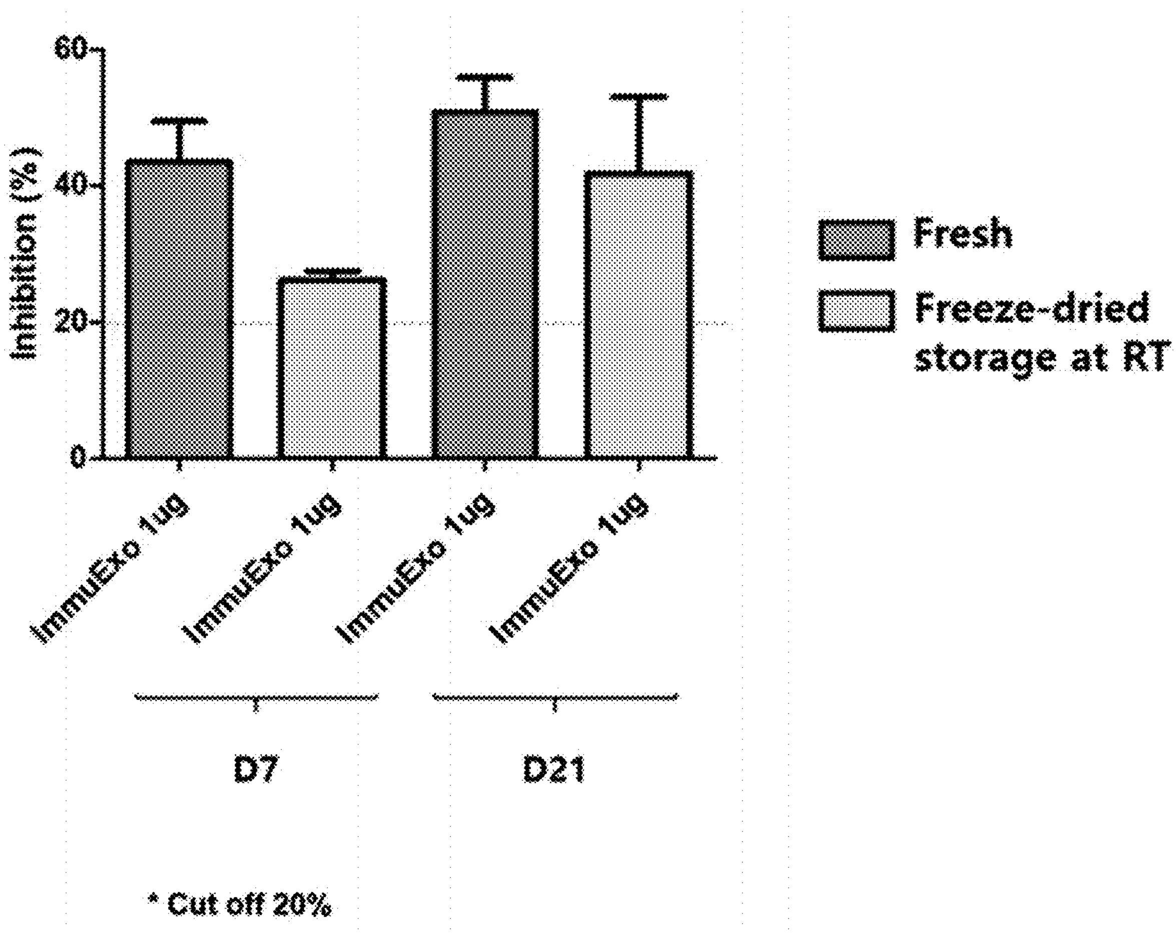

EXOSOMES COMPRISING CORONAVIRUS-DERIVED ANTIGEN PROTEIN OR GENE ENCODING SAME PROTEIN, AND USE OF SAME

TECHNICAL FIELD

The present invention relates to an extracellular vesicle including a coronavirus-derived antigen protein or a gene encoding the protein, and a use thereof.

BACKGROUND ART

A vaccine is a drug that imparts acquired immunity to a certain disease or pathogen to animals including humans, and has a structure similar to the antigen recognition site of a microbial pathogen mainly causing diseases. However, the vaccine is different from the pathogen in that it has no pathogenicity. In recent years, various types of vaccines for various pathogens and diseases have been developed, but there are still many diseases that require the development of more effective and safe vaccines.

Extracellular vesicles refer to nanovesicles that consist of a double lipid membrane and have a size of several tens to hundreds of nanometers, and are composed of biologically active substances such as proteins, lipids, genes, and the like. These extracellular vesicles typically include exosomes, ectosomes, microvesicles, or apoptotic bodies in addition to exosomes. In the related art, these extracellular vesicles have been considered to be debris secreted from cells. However, recently, as the clinical significance of extracellular vesicles has emerged, various studies have been conducted. In particular, exosomes, which are spherical vesicles discharged by the cells, contain various types of information such as proteins and DNA of parent cells. Accordingly, the development of cancer diagnostic markers and sensors using them as biomarkers is being actively conducted.

Exosomes refer to small membrane-structured vesicles (having a diameter of approximately 30 to 100 nm) secreted from various cells. As seen from studies through electron microscopy, it was observed that the exosomes do not separate directly from the plasma membrane, but originate from specific compartments inside the cells called multivesicular bodies (MVBs), and are released and secreted out of the cells. That is, when the fusion of MVBs and plasma membranes takes place, the vesicles are released into the extracellular environment, which are called exosomes. These exosomes are known to be produced and released in a living state from not only red blood cells but also various types of immune cells (including B-lymphocytes, T-lymphocytes, dendritic cells, platelets, and macrophages), tumor cells, stem cells, and the like.

Mammalian cell-derived exosomes are known to be involved in various physiological functions such as hemostasis, tissue regeneration, stem cell maintenance, inflammatory/immune response regulation, embryonic development, and the like. In particular, it has been reported that exosomes derived from immune cells may deliver inflammatory cytokines, or may directly or indirectly present an antigen to promote an immune response (Nat Rev Immunol. 2009 August; 9(8): 581-93). Based on the characteristics and in vivo functions of these exosomes, the exosomes are being researched and developed for use as nano-sized substance delivery systems, mediators and biomarkers in the fields of oncology, immunotherapy and regenerative medicine.

As such, studies are being conducted for use of the exosomes as a vaccine, but they are still limited to some diseases, and research and development of vaccine platform technology applicable to various diseases including infectious diseases is insufficient.

DISCLOSURE

Technical Problem

As a result of research efforts by the present inventors to develop an extracellular vesicle-based vaccine platform that is universally applicable to various diseases, it was confirmed that an extracellular vesicle acts as a potent immunostimulant and an antigen carrier to produce an antigen-specific neutralizing antibody and induce an antigen-specific T cell response. Therefore, the present invention is completed based on the results.

Therefore, it is an object of the present invention to provide an extracellular vesicle including a coronavirus-derived antigen protein or a gene encoding the protein.

It is another object of the present invention to provide a vaccine composition for preventing or treating a coronavirus infection, which includes the extracellular vesicle.

It is still another object of the present invention to provide a health functional food for preventing or improving a coronavirus infection, which includes the extracellular vesicle.

It is yet another object of the present invention to provide a method for preventing or treating a coronavirus infection, which includes administering the extracellular vesicle to a subject in need thereof.

It is yet another object of the present invention to provide a use of the extracellular vesicle for the manufacture of a drug for the prevention or treatment of a coronavirus infection.

However, the objects of the present invention are not limited to the objects described above, and other objects not described above will be clearly understood from the following description by those skilled in the art to which the present invention pertains.

Technical Solution

In order to solve the above problems, according to an aspect of the present invention, there is provided an extracellular vesicle including a coronavirus-derived antigen protein or a gene encoding the protein.

According to one embodiment of the present invention, the coronavirus may be severe acute respiratory syndrome-coronavirus-2 (SARS-CoV-2).

According to another embodiment of the present invention, the antigen protein may be the receptor binding domain (RBD) protein of the coronavirus-derived spike protein.

According to still another embodiment of the present invention, the antigen protein or the gene encoding the protein may be loaded into the extracellular vesicle.

According to yet another embodiment of the present invention, the extracellular vesicle may be derived from one or more selected from the group consisting of animal cells, plant cells, or microorganisms.

According to yet another embodiment of the present invention, the animal cells may include one or more cells selected from the group consisting of somatic cells, germ cells, immune cells, neurons, and tumor cells.

According to yet another embodiment of the present invention, the extracellular vesicle may be derived from activated immune cells.

According to yet another embodiment of the present invention, the extracellular vesicle may express one or more selected from the group consisting of CD63, CD81, and Flotillin 1.

According to another aspect of the present invention, there is provided a vaccine composition for preventing or treating a coronavirus infection, which includes the extracellular vesicle.

According to still another aspect of the present invention, there is provided a health functional food for preventing or improving a coronavirus infection, which includes the extracellular vesicle.

According to yet another aspect of the present invention, there is provided a method for preventing or treating a coronavirus infection, which includes administering the extracellular vesicles to a subject in need thereof.

According to yet another aspect of the present invention, there is provided a use of the extracellular vesicle for the manufacture of a drug for the prevention or treatment of a coronavirus infection.

Advantageous Effects

According to the present invention, when mice are immunized by administering an activated immune cell-derived extracellular vesicle loaded with an antigen protein or mRNA, excellent antigen-specific neutralizing antibody production and T cell response induction effects are confirmed. When the extracellular vesicle is stored under room-temperature and refrigerated conditions after freeze-drying, high stability and an excellent antibody production effect are experimentally confirmed. From these results, the extracellular vesicle according to the present invention or a vaccine composition including the same can serve as a platform applicable to various diseases with an excellent antigen-specific immune response induction effect and excellent stability, and thus is expected to be effectively used for the development of vaccines for preventing or treating various diseases including infectious diseases, particularly coronavirus infections.

DESCRIPTION OF DRAWINGS

FIG. 1 shows the results of confirming that THP-1 cells activated by treatment with LPS exhibit an M1 macrophage phenotype. Here, FIG. 1A is a micrograph showing resting THP-1 cells and activated THP-1 cells, and FIG. 1B shows the results of measuring the mRNA levels of pro-inflammatory cytokine markers IL-1β, IL-6, IL-8, TNF-α, and iNOS in each of the THP-1 cells.

FIG. 2 shows the results of analyzing the characteristics of exosomes isolated from activated THP-1 cells. Here, FIG. 2A shows the results of measuring diameters of the isolated exosomes through Nanosight tracking analysis (NTA), FIG. 2B is a transmission electron microscope (TEM) image showing the exosomes, and FIG. 2C shows the results of measuring the expression levels of exosome markers CD63, CD81, and Flotillin 1 protein by performing Western blotting using a cell lysate and isolated exosomes.

FIG. 3 shows the results of confirming whether an antibody is produced in mice immunized by administration of an activated THP-1 cell-derived exosome (COVID 19-ImmunExo) loaded with the RBD of the SARS-CoV-2-derived spike protein according to the present invention, or by administration of an adjuvant and the RBD protein together. Here, FIG. 3A is a schematic diagram showing an immunization experiment method and an analysis schedule for a mouse using the exosome, FIG. 3B shows the results of analyzing an antibody production effect by administering different concentrations of the exosome (ImmunExo) or by administering an adjuvant and the RBD protein (Adj+RBD 5 μg) together to mice and performing a SARS-CoV-2 sVNT test using a sample, which is obtained by 50-fold dilution of serum, after 7, 21, 30 and 50 days, and FIG. 3C shows the results of analyzing an antibody production effect by performing a SARS-CoV-2 SVNT test after isolated sera are diluted 10-fold and 50-fold, respectively, after 50 days in the same experimental groups as FIG. 3B.

FIG. 4 is a diagram showing the degree of antibody binding in a serum specific to the SARS-CoV-2 RBD of the immune cell (THP-1 cell or KG-1 cell)-derived exosomes loaded with the RBD protein or mRNA. Specifically, (1) FIG. 4A shows the results of measuring absorbance to analyze the degree of antibody binding in the serum specific to the SARS-CoV-2 RBD after different concentrations of THP-1 cell-derived exosomes were administered, or an adjuvant and the RBD protein are administered together to the mice of each experimental group and the sera are isolated after 50 days in the same manner as in FIG. 3C, 2) FIG. 4B shows the results of measuring absorbance to analyze the degree of antibody binding in the serum specific to the SARS-CoV-2 RBD after THP-1 cell-derived exosomes are administered, or an adjuvant and the RBD protein are administered together, and the sera are isolated after 7 days, 3) FIG. 4C shows the results of measuring absorbance to analyze the degree of antibody binding in the serum specific to the SARS-CoV-2 RBD after THP-1 cell-derived exosomes are administered, or the adjuvant and RBD protein are administered together, and the sera are isolated after 7 and 14 days, and 4) FIG. 4D shows the results of measuring absorbance to analyze the degree of antibody binding in the serum specific to the SARS-CoV-2 RBD after KG-1 cell-derived exosomes are administered, or the adjuvant and RBD mRNA are administered together, and the sera are isolated after 7 and 14 days.

FIG. 5 shows the results of isolating splenocytes from mice immunized by administration of activated THP-1 cell-derived exosomes (ImmunExo) loaded with the RBD of the SARS-CoV-2-derived spike protein, or by administration of an adjuvant and the RBD protein together, and performing an IFN-γ enzyme-linked immunospot (ELISPOT) assay on the splenocytes. Here, FIG. 5A shows the results of confirming whether spots are produced after the IFN-γ ELISPOT assay is performed, and a quantification graph of the number of spots, and FIG. 5B shows the results of measuring an IFN-γ protein level by performing ELISA using a splenocyte culture medium.

FIG. 6 shows the results of confirming the stability of activated THP-1 cell-derived exosomes loaded with the RBD of the SARS-CoV-2-derived spike protein according to the present invention according to the storage of the activated THP-1 cell-derived exosomes. Here, FIG. 6A is a schematic diagram showing an experimental schedule for analyzing an effect of the exosomes, FIG. 6B shows the comparison of antibody production effects between exosomes stored at 4° C. for 7 days after freeze-drying and intact exosomes (fresh) not stored after freeze-drying by administering 0.1, 0.5, or 1 μg of the exosomes stored after freeze-drying to each of mice to immunize the mice and obtaining each of the sera at 7 and 21 days after the administration to perform a SARS-CoV-2 sVNT test, and FIG. 6C shows the comparison of antibody production effects between the exosomes stored at room temperature for 7 days after freeze-drying and intact exosomes (fresh) not stored after freeze-drying by administering 1 μg of the exosomes stored after freeze-drying to mice to immunize the mice and obtaining each of the sera at 7 and 21 days after the administration to perform a SARS-CoV-2 sVNT test.

BEST MODE

The present invention relates to vaccine platform technology that may be effectively used in the field of vaccine development for prevention or treatment of various infectious diseases using an extracellular vesicle functioning as a potent immunostimulant and an antigen carrier.

Hereinafter, the present invention will be described in detail.

The present invention provides an extracellular vesicle including a coronavirus-derived antigen protein or a gene encoding the protein.

According to the present invention, the coronavirus may be severe acute respiratory syndrome-coronavirus-2 (SARS-CoV-2).

Also, according to the present invention, the antigen protein may be the receptor binding domain (RBD) protein of the coronavirus-derived spike protein, and the gene encoding the antigen protein may be a nucleic acid encoding the receptor binding domain (RBD) protein of the coronavirus-derived spike protein. Also, the nucleic acid may be DNA, RNA, or a combination thereof.

In addition, according to the present invention, the antigen protein or the gene encoding the protein may be loaded into the extracellular vesicle.

A method of loading the antigen protein or the gene encoding the protein into the extracellular vesicle is not particularly limited, and methods known in the art may be properly selected and used by those skilled in the art.

As used herein, the term "antigen" refers to a molecule capable of inducing an immune response to generate an antibody in a host subject. In this case, the antigen is a target of the antibody, and each antibody is produced in an antigen-specific manner in order to respond to an antigen after the cells of the immune system come into contact with the antigen. According to the present invention, when the antigen is in a form capable of inducing an immune response as described above, it includes all of proteins, genes encoding the proteins, and mRNA forms of the genes. In this case, the origin of the antigen is not particularly limited. Non-limiting examples of the antigen may include all types of antigens derived from microorganisms including viruses, bacteria or fungi, and those derived from cancer cells.

As used herein, the term "extracellular vesicle" refers to a small sphere surrounded by a membrane derived from cells. The name of these spheres varies greatly depending on the origin of a cell from which it is made or a method by which it is made. According to the present invention, the extracellular vesicle may include one or more selected from the group consisting of exosomes, ectosomes, microvesicles, and apoptotic bodies, which are named according to the method of making the same in cells, and may particularly be exosomes, but the present invention is not limited thereto.

The extracellular vesicle may be an extracellular vesicle derived from a natural organism, for example, an extracellular vesicle derived from one or more selected from the group consisting of animals, plants and microorganisms, or an artificially produced extracellular vesicle. Also, the cells may be cells isolated from a natural organism. In addition, the cells may be derived from any type of animal or plant, including humans and non-human mammals. The animal cells may include one or more cells selected from the group consisting of somatic cells, germ cells, immune cells, neurons, and tumor cells.

Also, the extracellular vesicle may be derived from activated immune cells, and may be specifically derived from activated THP-1 cells or KG-1 cells. In this case, the activation may be realized by lipopolysaccharide (LPS). When THP-1 cells are activated, the THP-1 cells may express one or more proteins selected from the group consisting of IL-1β, IL-6, IL-8, TNF-α, and iNOS while changing their cell morphology similar to macrophages.

According to one specific embodiment of the present invention, for example, the phenotypic change of immune cells activated through antigen stimulation was analyzed, and the characteristics of exosomes isolated therefrom were observed.

Specifically, according to one embodiment of the present invention, when THP-1 cells (i.e., a human monocyte cell line) are treated with lipopolysaccharide (LPS), the morphology of the cells is changed and markers for M1 macrophages are expressed when compared to cells which are not treated with LPS (see Example 1).

The somatic cells are cells that constitute the body of any type of animal including mammals including humans. In the present invention, the somatic cells may include all types of cells other than germ cells, immune cells, neurons, and tumor cells.

The immune cells refer to cells that determine the immune response in the body, that is, cells that serve to defend against invading pathogens, foreign substances, viruses, and the like, control immunity and remove cancer cells constantly produced in the body. Specifically, the immune cells may include natural killer cells (NK cells), dendritic cells, T cells, B cells, macrophages and lymphocytes, but the present invention is not limited thereto.

The neurons refer to cells that constitute the nervous system, that is, cells that may express ion channels such as sodium and potassium channels to transmit signals in an electrical manner unlike other cells and exchange various types of information by exchanging chemical signals with other adjacent neurons through a structure called a synapse. In the present invention, the specific type of the neurons is not limited, and may include all types of cells that secrete the extracellular vesicles.

The tumor cells are used with the same meaning as cancer cells, and refer to cells whose cell cycle is not regulated unlike normal cells, resulting in rapid and irregular growth of the cells. In the present invention, the origin of the tumor cells is not particularly limited, and the tumor cells may include all types of tumor cells that secrete extracellular vesicles.

Also, according to one embodiment of the present invention, the extracellular vesicle may express one or more selected from the group consisting of CD63, CD81, and Flotillin 1, and may particularly express all of CD63, CD81, and Flotillin 1.

According to another embodiment of the present invention, it was confirmed that the activated immune cell-derived exosome, preferably an activated TH-1 cell-derived exosome has an average diameter of 154.0 nm, and expresses exosome marker proteins of CD63, CD81, and Flotillin 1 (see Example 2).

Also, the present invention provides a vaccine composition for preventing or treating a coronavirus infection, which includes the extracellular vesicle.

The terms "extracellular vesicle," "coronavirus," "antigen," and the like are as described above.

As used in the present invention, the term "prevention" refers to any action that suppresses or delays the onset of a specific disease or disorder by administration of the vaccine composition according to the present invention.

As used in the present invention, the term "treatment" refers to any action in which the symptoms for a specific disease or condition are improved or changed advantageously by administration of the vaccine composition according to the present invention.

As used in the present invention, the term "vaccine" is intended to include all types of actions of preventing infection or reinfection by a corresponding pathogen or antigen, reducing the severity of symptoms or eliminating the symptoms, or substantially or completely eliminating a disease caused by the corresponding pathogen or antigen by inducing an immune response against the corresponding antigen in a host including humans. Therefore, the vaccine composition of the present invention is preferably prophylactically administered to a subject prior to infection with the corresponding pathogen or the onset of a disease, and may also be administered therapeutically after infection with the corresponding pathogen or the onset of the disease.

According to one embodiment of the present invention, the activated THP-1 cell- or KG-1 cell-derived exosome loaded with the receptor binding domain (RBD) protein or mRNA of the SARS-CoV-2-derived spike protein was prepared, immunization was performed by subcutaneous administration to mice, and whether a neutralizing antibody was produced was confirmed. As a result, it was confirmed that the activated THP-1 cell- or KG-1 cell-derived exosome shows similar levels of RBD-specific IgG and neutralizing antibody titers even at a much smaller amount compared to when the RBD protein or mRNA are administered together with an adjuvant (see Examples 3 to 5).

Also, according to the present invention, the vaccine composition may induce antigen-specific antibody production and a T cell-mediated immune response at the same time.

According to another embodiment of the present invention, splenocytes were separated from the mice immunized by administration of the exosome to analyze an RBD antigen-specific T cell response. As a result, it was confirmed that a T cell response is not induced in the mice to which the RBD is administered together with an adjuvant, but a potent T cell response is induced in the mice immunized with the exosomes (see Example 6).

Also, according to the present invention, the vaccine composition may be freeze-dried.

The present inventors confirmed the specific immune response induction effect and the storage stability of the vaccine composition through Examples. Specifically, to evaluate the storage stability of the exosome according to the present invention, a freeze-dried exosome (COVID19-ImmunExo) was stored for 7 days under a refrigerated condition of 4° C., or stored at room temperature, and mice were then subcutaneously immunized to analyze whether the antibody is produced. As a result, it was confirmed that excellent stability and an excellent antibody production effect are maintained even after the exosome is stored under the above conditions (see Example 7).

The immune cell-derived exosomes activated through Examples of the present invention show lymph node orientation after subcutaneous injection. Because the immune cell-derived exosomes are mainly taken up by local macrophages and dendritic cells, an MHC-I/peptide complex is observed in exosomes by dendritic cells. Based on results, it can be seen that immune cell-derived exosomes may more effectively produce neutralizing antibodies against SARS-CoV-2, and may also induce an RBD-specific T cell response in splenocytes of the immunized mice.

Therefore, in the present invention, the results confirmed in Examples suggest that nano-sized extracellular vesicles including exosomes secreted from the cells can become a platform capable of acting as a potent immunostimulant and an antigen carrier to design an effective vaccine against target diseases.

The vaccine composition of the present invention may be prepared in any suitable form of a pharmaceutically acceptable formulation. For example, the vaccine composition may be prepared in the form of a solution or suspension for extemporaneous administration, in the form of a concentrated stock solution suitable for dilution prior to administration, or in a reconstitutable form such as freeze-dried, lyophilized, or frozen formulations.

The vaccine composition of the present invention may be formulated so that the vaccine composition further includes a pharmaceutically acceptable carrier. Specifically, the carrier may, for example, include a colloidal suspension, a powder, saline, a lipid, liposomes, microspheres, or nanospherical particles. They may form a complex with a vehicle or may be associated with the vehicle. In this case, they may be delivered in vivo using delivery systems known in the art, such as lipids, liposomes, microparticles, gold, nanoparticles, polymers, condensation reagents, polysaccharides, polyamino acids, dendrimers, saponins, adsorption enhancing substances or fatty acids.

Also, the pharmaceutically acceptable carrier will usually include a diluent, an excipient, a stabilizer, a preservative, and the like. Suitable diluents include non-aqueous solvents such as propylene glycol, polyethylene glycol, vegetable oils (e.g., olive oil, peanut oil), and the like, or aqueous solvents such as saline (preferably, 0.8% saline), water containing a buffered medium (preferably, a 0.05 M phosphate buffer), and the like. Suitable excipients include starch, glucose, lactose, sucrose, gelatin, malt, rice, wheat flour, chalk, silica gel, sodium stearate, glycerol monostearate, talc, sodium chloride, anhydrous skim milk, glycerol, propylene, glycol, water, ethanol, and the like. Suitable stabilizers include carbohydrates such as sorbitol, mannitol, starch, sucrose, dextran, glutamate, glucose, and the like, or proteins including animal, vegetable or microbial proteins such as milk powder, serum albumin, casein, and the like. Suitable preservatives include thimerosal, merthiolate, gentamicin, neomycin, nystatin, amphotericin B, tetracycline, penicillin, streptomycin, polymyxin B, and the like.

The vaccine composition of the present invention may further include an antigen adjuvant. The antigen adjuvant may consist of one or more substances that enhance an immune response against antigens. For example, the antigen adjuvant may be Freund's complete adjuvant, Freund's incomplete adjuvant, a saponin, a gel-phase aluminum adjuvant, a surface active substance (e.g., lysolecithin, plurone glycol, a polyanion, a peptide, an oil, a hydrocarbon emulsion, or the like), a vegetable oil (e.g., cottonseed oil, peanut oil, corn oil, or the like), vitamin E acetate, and the like.

The vaccine composition of the present invention may be prepared using a method commonly used in the art to which the present invention pertains. The vaccine composition may be prepared as an oral or parenteral formulation. In this case, the parenteral formulation may be preferably administered via any one route of administration selected from the group consisting of transdermal, intramuscular, intraperitoneal, intravenous, subcutaneous, nasal, or epidural routes.

The term "administration" refers to an action of introducing a predetermined substance into a subject using a suitable method, and the term "subject" refers to any living organism including a human, a mouse, a rat, livestock, and the like, capable of having a coronavirus infection. A specific example may be a mammal including a human.

The vaccine composition of the present invention is administered in a pharmaceutically effective amount. As used in the present invention, the term "pharmaceutically effective amount" refers to an amount sufficient to exhibit a vaccine effect, that is, an amount that does not cause side effects nor produce a serious or excessive immune response. In this case, a level of the effective dose varies depending on various factors including a disorder to be treated, the severity of the disorder, the activity of a vaccine substance, a route of administration, the rate of protein clearance, the duration of treatment, the substance used in combination with or concurrently with the vaccine composition, the age, weight, sex, diet, general health condition of the subject, and other factors known in the medical field.

Also, the present invention provides a health functional food for preventing or improving a coronavirus infection, which includes the extracellular vesicle.

The terms "extracellular vesicle," "coronavirus," "prevention," and the like are as described above.

The term "improvement" may refer to all actions of reducing at least the severity of parameters, for example, symptoms associated with the condition to be treated. In this case, the health functional food may be used simultaneously with or separately from a therapeutic drug before or after the onset of the corresponding disease in order to prevent or ameliorate a coronavirus infection.

In the health functional food, the active ingredient may be added to foods as is, or used together with other foods or food ingredients. In this case, the active ingredient may be properly used according to conventional methods. The mixing amount of the active ingredient may be properly determined depending on the purpose of use (for prevention or improvement). In general, the health functional food may be specifically added in an amount of about 15% by weight or less, more specifically about 10% by weight or less with respect to the raw materials during the preparation of foods or beverages. However, when the health functional food is taken for an extended period for the purpose of health and hygiene or for the purpose of health control, the amount may be above or below the above range.

The health functional food further includes one or more of a carrier, a diluent, an excipient, and an additive, and may be formulated as any one selected from the group consisting of a tablet, a pill, a powder, a granule, a powder, a capsule, and a liquid formulation. Foods to which the exosome according to one embodiment may be added include various foods, powders, granules, tablets, capsules, syrups, beverages, gums, teas, vitamin complexes, health functional foods, and the like.

Specific examples of the carrier, the excipient, the diluent, and the additive may include at least one selected from the group consisting of lactose, dextrose, sucrose, sorbitol, mannitol, erythritol, starch, gum acacia, calcium phosphate, alginate, gelatin, calcium phosphate, calcium silicate, microcrystalline cellulose, polyvinylpyrrolidone, cellulose, methylcellulose, water, sugar syrup, methylcellulose, methyl hydroxybenzoate, propyl hydroxybenzoate, talc, magnesium stearate and mineral oil.

The health functional food may contain other ingredients as essential ingredients without any particular limitation in addition to containing the active ingredient. For example, as in conventional beverages, the health functional food may contain various flavoring agents or natural carbohydrates as additional ingredients. Examples of the above-described natural carbohydrates include monosaccharides such as glucose, fructose, and the like; disaccharides such as maltose, sucrose, and the like; and polysaccharides, for example, conventional sugars such as dextrin, cyclodextrin, and the like, and sugar alcohols such as xylitol, sorbitol, erythritol, and the like. Other than the flavoring agents described above, natural flavoring agents (thaumatin, a stevia extract (e.g., rebaudioside A, glycyrrhizin, and the like)), and synthetic flavoring agents (saccharin, aspartame, and the like) may be advantageously used. The proportion of the natural carbohydrate may be properly determined through the selection of those skilled in the art.

In addition, the health functional food according to one aspect includes various nutrients, vitamins, minerals (electrolytes), flavoring agents such as synthetic and natural flavoring agents, coloring agents and thickening agents (cheese, chocolate, and the like), pectic acid and salts thereof, alginic acid and salts thereof, organic acids, protective colloidal thickeners, pH adjusters, stabilizers, preservatives, glycerin, alcohols, carbonation agents used in carbonated beverages, and the like. These components may be used alone or in combination, and the proportion of these additives may also be properly selected by those skilled in the art.

Also, the present invention provides a method for preventing or treating a coronavirus infection, which includes administering the extracellular vesicle to a subject in need thereof.

The terms "extracellular vesicle," "subject," "administration," "coronavirus infection," "prevention," "treatment," and the like are as described above.

Further, the present invention provides a use of the extracellular vesicle for the manufacture of a drug for the prevention or treatment of a coronavirus infection.

The terms "extracellular vesicle," "coronavirus infection," "prevention," "treatment," and the like are as described above.

MODE FOR INVENTION

Hereinafter, preferred embodiments of the present invention are presented to aid in understanding the present invention. However, it should be understood that the following Examples are only provided for easier understanding of the present invention, and are not intended to limit the scope of the present invention.

EXAMPLES

Example 1. Observation of Phenotype of Activated Immune Cells

To develop a vaccine using an extracellular vesicle, the present inventors attempted to prepare a vaccine using exosomes isolated from activated immune cells by first selecting immune cells and stimulating the immune cells with an antigen. For this purpose, as one example of the immune cells, THP-1 cells, which are a human monocyte cell line, were activated to observe the phenotype of the activated cells.

Figure 1B:
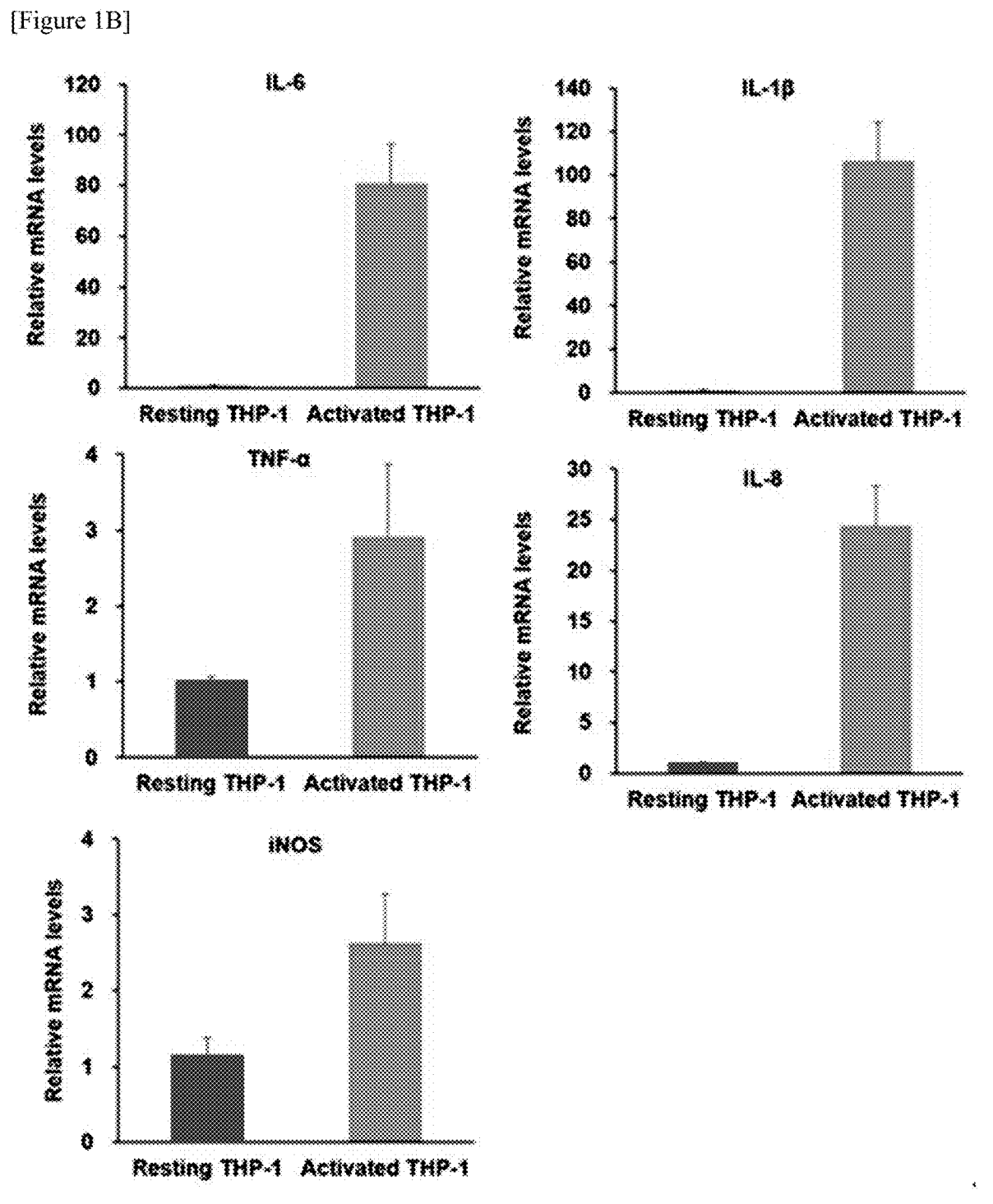

Specifically, THP-1 cells ($8\times10^5$ cells/mL) were treated with 100 ng/ml of lipopolysaccharide (LPS) to activate the cells. Thereafter, the cell morphologies of the treated THP-1 cells and resting THP-1 cells not treated with LPS were observed. As a result, as shown in FIG. 1A, it was confirmed that the cell morphology of the activated THP-1 cells was changed in a manner similar to macrophages when compared to the resting THP-1 cells.

Further, based on the above results, the mRNA levels of pro-inflammatory cytokine markers IL-1β, IL-6, IL-8, TNF-α, and iNOS secreted by M1 macrophages were measured to check whether the THP-1 cells activated by the LPS treatment differentiated into M1 macrophages, as reported in the related art. As a result, as shown in FIG. 1B, it was confirmed that the markers were hardly expressed in the case of the resting THP-1 cells, whereas the expression of the markers increased, and particularly, the mRNA levels of IL-1β, IL-6, and IL-8 significantly increased in the case of the activated THP-1 cells.

Based on the above results, it can be seen that the THP-1 cells activated through the LPS treatment exhibited the M1 macrophage phenotype.

Example 2. Characterization of Activated Immune Cell-Derived Exosomes

To confirm the characteristics of the activated THP-1 cell-derived exosome, the present inventors isolated exosomes from the cells through the following process. Specifically, a supernatant was collected by centrifuging a cell culture medium at 1,200 rpm for 5 minutes to remove cells and cell debris. Thereafter, the collected supernatant was passed through a 0.2 μm filter to remove microparticles larger than exosomes. Then, the exosomes were concentrated and washed using a Tangential flow filtration (TFF) system.

Next, the characteristics of the isolated exosomes were analyzed through Nanosight tracking analysis (NTA) and transmission electron microscope observation. As a result, as shown in FIGS. 2A and 2B, it was confirmed that the isolated exosomes had an average diameter of 154.0 nm and a circular shape.

Also, it was confirmed that the concentration of the isolated exosomes was $2.6\times10^{11}$ particles/mL, and the concentration of the exosome protein was 3.5 mg/mL when it was quantitatively analyzed through a BCA assay. Furthermore, in order to examine whether the isolated exosomes expressed an exosome marker, Western blotting was performed using a cell lysate and the isolated exosomes to measure the expression levels of exosome markers CD63, CD81, and Flotillin 1. As a result, as shown in FIG. 2C, it was confirmed that only CD63 was expressed at a weak level in the cell lysate, but all of the marker proteins were expressed at a high level in the isolated exosomes.

Based on the above results, it can be clearly seen that the exosomes isolated from the activated THP-1 cells were exosomes having the characteristics described above.

Example 3. Preparation of Exosomes Loaded with Recombinant SARS-CoV-2-Derived Protein The present inventors attempted to load the activated THP-1 cell- or KG-1 cell-derived exosomes isolated in Example 2 with the receptor binding domain (RBD) protein of the SARS-CoV-2-derived spike protein to verify the prophylactic effect as a vaccine against SARS-CoV-2 infection.

For this purpose, a protein construct (Cat. No. Ab-P0018, AbClon) in which a DNA sequence encoding the RBD (YP_009724390.1) (Ser325-Lys529) of the SARS-CoV-2-derived spike protein was first fused with an Fc region of mouse IgG2a at the C-terminus thereof was prepared. Thereafter, in order to load the activated THP-1 cell- or KG-1 cell-derived exosomes with the RBD protein expressed from the construct, $3\times10^{11}$ (9 mg) exosomes and 300 μg of RBD protein were prepared, and treated with extracorporeal shockwaves (ESWs). Then, the RBD protein-loaded exosomes were washed and concentrated using an ultracentrifuge (at 32,000 rpm for 2 hours).

Next, the amount of RBD protein loaded into the THP-1 cell-derived exosome was quantitatively analyzed using ELISA. As a result, it was confirmed that a total of 40.754 μg of RBD protein was loaded into the exosome. The present inventors attempted to evaluate an effect of the activated THP-1 cell- or KG-1 cell-derived exosomes (ImmunExo RBD or COVID 19-ImmunExo) prepared above, which were loaded with the RBD of the SARS-CoV-2-derived spike protein, on SARS-CoV-2 infection (COVID-19) using the following experiments.

Example 4. Preparation of Exosomes Loaded with Recombinant SARS-CoV-2-Derived mRNA The present inventors attempted to load the activated THP-1 cell- or KG-1 cell-derived exosomes isolated in Example 2 with the receptor binding domain (RBD) mRNA of the SARS-CoV-2-derived spike protein to verify the prophylactic effect as a vaccine against SARS-CoV-2 infection.

Specifically, RBD mRNA was prepared from a DNA template through an in vitro transcription (IVT) process. For the prepared RBD mRNA, the THP-1 cell- or KG-1 cell-derived exosomes (9 mg) and 150 μg of RBD mRNA were prepared, and treated with extracorporeal shockwaves (ESWs). Then, the RBD protein-loaded exosomes were washed and concentrated using an ultracentrifuge (at 32,000 rpm for 2 hours).

Next, the amount of RBD mRNA loaded into the THP-1 cell- or KG-1 cell-derived exosome was quantitatively analyzed using qRT-PCR. As a result, it was confirmed that a total of 81 μg and 64.5 μg of RBD protein were loaded into the THP-1 cell-derived exosome and the KG-1 cell-derived exosome, respectively. The present inventors attempted to evaluate an effect of the activated THP-1 cell- or KG-1 cell-derived exosomes (Exo+RBD mRNA) prepared above, which were loaded with the RBD mRNA of the SARS-CoV-2-derived spike protein, on SARS-CoV-2 infection (COVID-19) using the following experiments.

Example 5. Confirmation of Vaccine Efficacy of Activated Immune Cell-Derived Exosomes Against COVID-19

The present inventors evaluated the efficacy of the activated THP-1 cell- or KG-1 cell-derived exosomes prepared in Example 3, which were loaded with the RBD protein or mRNA of the SARS-CoV-2-derived spike protein, as a vaccine against COVID-19.

For this purpose, an in vivo immunization experiment was performed using mice according to the schedule shown in FIG. 3A. Specifically, various concentrations (0.005, 0.01, 0.05, 0.1, 0.2, 0.5 or 1 μg) of the activated THP-1 cell-derived exosomes (COVID 19-ImmunExo, or ImmunExo) loaded with the RBD protein of the spike protein were injected into the corresponding mice. In this case, the same number of exosome particles was injected. As the control, an adjuvant and the RBD protein were administered together to the mice (Adj+RBD). Here, 500 μg of $Al(OH)_3$ serving as the adjuvant was administered per mouse, and 5 μg of RBD protein was administered per mouse. Thereafter, the effects of the exosomes were evaluated in various aspects through the following experiments.

Also, the activated KG-1 cell-derived exosomes (COVID 19-ImmunExo, or ImmunExo) loaded with the RBD protein of the spike protein were subcutaneously injected at a concentration of 1 μg, and the activated THP-1 cell- or KG-1 cell-derived exosome (Exo+RBD mRNA) loaded with the RBD mRNA of the spike protein were subcutaneously injected at a concentration of 10 μg. In this case, the same number of exosome particles was injected. As the control, an adjuvant and the RBD protein or mRNA were administered together to the mice (Adj+RBD or Adj+RBD mRNA). Here, 500 μg of $Al(OH)_3$ serving as the adjuvant was administered per mouse, and 5 μg and 10 μg of RBD protein and RBD mRNA were administered per mouse, respectively. Thereafter, the effects of the exosomes were evaluated in various aspects through the following experiments.

5-1. SARS-CoV-2 Surrogate Virus Neutralization Test (sVNT)

A SARS-CoV-2 surrogate virus neutralization test is a test based on the effect of a neutralizing antibody on the interaction between the RBD of SARS-CoV-2 and the human ACE2 (hACE2) receptor protein using a blocking ELISA detection system that mimics a virus neutralization process. The detection sensitivity of the test was 93.80%, and the inhibition efficiency (inhibition %) for the interaction was derived through Equation 1 below. The cutoff of the result values was made based on 20%. When the result value was greater than 20%, it was construed as a positive value indicating that the neutralizing antibody against SARS-CoV-2 was detected. On the other hand, when the result value was less than 20%, it was construed that the neutralizing antibody was not detected.

$$\text{Inhibition} = \left(1 - \frac{\text{OD value of Sample}}{\text{OD value of Negative Control}}\right) \times 100\% \quad \text{[Equation 1]}$$

Accordingly, the activated THP-1 cell-derived exosomes (COVID 19-ImmunExo) loaded with the RBD protein of the SARS-CoV-2-derived spike protein were administered at different concentrations, or an adjuvant and the RBD protein were administered together to the mice (Adj+RBD 5 μg), as described above. Thereafter, blood was collected at 7, 21, 30, and 50 days, and the serum was then diluted 50-fold (×50 dilution), and the inhibitory efficiency was calculated through the above equation.

As a result, as shown in FIG. 3B, it was confirmed that the inhibitory efficiency increased in proportion to the administered concentration when the exosomes (ImmunExo) was administered, and when 1 μg of the exosomes were administered, the inhibitory efficiency was observed at a level very similar to the inhibitory efficiency when the adjuvant and RBD protein were administered together.

Based on the above results, sera was isolated from collected blood after 50 days, and diluted 10-fold and 50-fold, respectively, to obtain samples. Then, the inhibitory efficiency was analyzed for each of the samples. As a result, as shown in FIG. 3C, it was confirmed that when 1 μg of the exosomes were administered, the inhibitory efficiency was also observed at a level very similar to the inhibitory efficiency when the adjuvant and 5 μg of RBD protein were administered together.

5-2. Analysis of Serum Antibody Response to SARS-CoV-2

(1) In Case of THP-1 Cell-Derived Exosomes Loaded with RBD Protein of SARS-CoV-2-Derived Spike Protein The present inventors measured absorbance to analyze the degree of antibody binding in the serum specific to the RBD of SARS-CoV-2 by obtaining a serum sample after 50 days from each of the mice to which the activated THP-1 cell-derived exosomes (ImmunExo) loaded with the RBD protein of the SARS-CoV-2-derived spike protein were administered at different concentrations, or each of the mice to which the adjuvant and RBD protein were administered together, described in Example 5-1, and then diluting the serum sample with PBS supplemented with 1% BSA at a ratio of 1:100 to 1:1,000.

As a result, as shown in FIG. 4A, it was confirmed that the degree of antibody binding decreased in the same manner as the mouse-derived serum was diluted and was generally proportional to the administered concentration of the exosomes, in all the experimental groups. Also, it was confirmed that overall antibody binding was observed to be highest when 1 μg of the exosomes were administered, and when 0.5 μg of the exosomes were administered, the overall antibody binding was observed to be similar to those of the groups (Adj+RBD 5 μg) in which the adjuvant and RBD protein were administered together.

(2) In Case of KG-1 Cell-Derived Exosomes Loaded with RBD Protein of SARS-CoV-2-Derived Spike Protein The present inventors measured absorbance to analyze the degree of antibody binding in the serum specific to the RBD of SARS-CoV-2 by obtaining a serum sample after 7 days from each of the mice prepared in Example 3 to which the activated THP-1 cell-derived exosomes (ImmunExo) loaded with the RBD protein of the SARS-CoV-2-derived spike protein were administered at a concentration of 1 μg, or each of the mice prepared in Example 3 to which the adjuvant and 1 μg of RBD protein were administered together, and then diluting the serum sample with PBS supplemented with 1% BSA at a ratio of 1:100 to 1:1,000.

As a result, as shown in FIG. 4B, it was confirmed that degree of antibody binding in the serum specific to the RBD of SARS-CoV-2 was observed compared to the control.

(3) In Case of THP-1 Cell-Derived Exosomes Loaded with RBD mRNA of SARS-CoV-2-Derived Spike Protein The present inventors measured absorbance to analyze the degree of antibody binding in the serum specific to the RBD of SARS-CoV-2 by obtaining a serum sample after 7 and 14 days from each of the mice prepared in Example 4 to which the activated THP-1 cell-derived exosomes (ImmunExo) loaded with the RBD mRNA of the SARS-CoV-2-derived spike protein were administered at a concentration of 10 μg, or each of the mice prepared in Example 4 to which the adjuvant and 10 μg of the RBD mRNA were administered together, and then diluting the serum sample with PBS supplemented with 1% BSA at a ratio of 1:100 to 1:1,000.

As a result, as shown in FIG. 4C, it can be seen that the degree of antibody binding in the serum specific to the RBD of SARS-CoV-2 could not be measured after 7 days, but the degree of antibody binding in the serum specific to the RBD of SARS-CoV-2 was observed after 14 days to be significantly higher than those of the control and the group to which the adjuvant and RBD mRNA were administered together (4) In Case of KG-1 Cell-Derived Exosomes Loaded with RBD mRNA of SARS-CoV-2-Derived Spike Protein The present inventors measured absorbance to analyze the degree of antibody binding in the serum specific to the RBD of SARS-CoV-2 by obtaining a serum sample after 7 and 14 days from each of the mice prepared in Example 4 to which the activated KG-1 cell-derived exosomes (Exo+RBD mRNA) loaded with the RBD mRNA of the SARS-CoV-2-derived spike protein were administered at a concentration of 10 μg, or each of the mice prepared in Example 4 to which the adjuvant and 10 μg of the RBD mRNA were administered together, and then diluting the serum sample with PBS supplemented with 1% BSA at a ratio of 1:100 to 1:1,000.

As a result, as shown in FIG. 4D, it can be seen that the degree of antibody binding in the serum specific to the RBD of SARS-CoV-2 was measurable after 7 days only for the group of the activated KG-1 cell-derived exosomes (Exo+RBD mRNA) loaded with the RBD mRNA of the SARS-CoV-2-derived spike protein, unlike the other groups, and the degree of antibody binding in the serum specific to the RBD of SARS-CoV-2 was observed after 14 days to be significantly higher than the control and the group to which the adjuvant and RBD mRNA were administered together.

5-3. Analysis of SARS-CoV-2 RBD-Specific T Cell Response

The present inventors attempted to isolate splenocytes from the mice immunized in Example 5-1 by administering the activated THP-1 cell-derived exosomes (ImmunExo) loaded with the RBD protein of the SARS-CoV-2-derived spike protein and perform an IFN-γ enzyme-linked immunospot (ELISPOT) assay on the splenocytes to analyze a SARS-CoV-2 RBD-specific T cell response. The IFN-γ ELISPOT assay is a sensitive technique for detecting antigen-specific T cells that secrete cytokines at the single cell level, and is useful for monitoring the effect of a vaccine that induces cell-mediated immunity because it may directly measure the Th1 cell-mediated immune response. Also, the IFN-γ ELISPOT assay may directly measure the frequency of cytokine-producing T cells by determining the number of spots generated through a colorimetric reaction.

To perform the assay, splenocytes derived from each of the mice in Example 5-1 were seeded into each well of a plate at $5\times10^5$/well, and the RBD protein of the SARS-CoV-2-derived spike protein was treated at 2 μg/mL, and then cultured for 24 hours.

As a result, as shown in FIG. 5A, it was confirmed that no spots appeared in the group (Adj+RBD 5 μg) to which the adjuvant and RBD protein were administered, but the number of spots differed depending on the administered concentration of the exosomes in the group to which the exosomes (COVID19-ImmunExo) according to the present invention were administered, and the spots appeared to be produced. In particular, it was confirmed that the highest number of spots appeared in the group to which 0.5 μg of the exosomes were administered.

Further, after the mouse-derived splenocytes ($1\times10^7$/well) to which the exosomes according to the present invention were administered or the adjuvant and RBD protein were administered together were treated with 2 μg/mL of RBD protein of the SARS-CoV-2-derived spike protein for 48 hours in the same manner as above, ELISA was performed using the culture medium of the splenocytes to measure a level of the IFN-γ protein secreted from the Th1 cells.

Figure 5B:
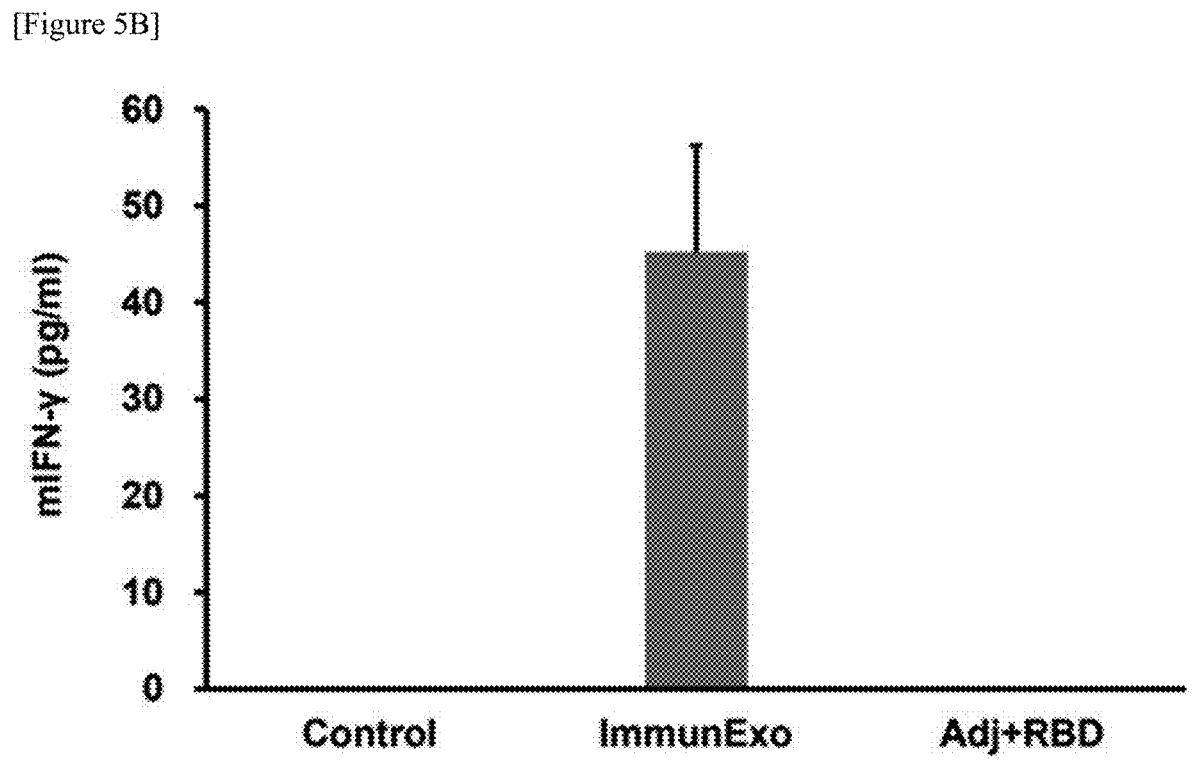

As a result, as shown in FIG. 5B, it was confirmed that no IFN-γ was present at all in the culture medium of the mouse-derived splenocytes to which the adjuvant and RBD protein were administered together, but IFN-γ was present in the culture medium of the mouse-derived splenocytes to which the exosomes (ImmunExo) according to the present invention were administered, which was consistent with the results of FIG. 5A.

The above results suggest that a Th1 cell-mediated immune response was not induced when the adjuvant and RBD protein were administered together, but a Th1 cell-mediated immune response was strongly induced by the administration of the exosomes according to the present invention.

Example 6. Verification of Storage Stability and Effectiveness of Freeze-Dried COVID19-ImmunExo In order to confirm the clinical applicability of the activated THP-1 cell-derived exosomes (COVID19-ImmunExo) loaded with the RBD protein of the SARS-CoV-2-derived spike protein according to the present invention, the present inventors verified the storage stability of the exosomes.

More specifically, the exosomes of the present invention freeze-dried according to the schedule shown in FIG. 6A were prepared at a single dose concentration, divided into tubes, frozen at −70° C. for one day, and then freeze-dried. Thereafter, the freeze-dried exosomes were stored for 7 days at 4° C. (FIG. 6B) or at room temperature (FIG. 6C), and the exosomes prepared in a dosage form were then administered to each mice at the given concentrations. Then, a SARS-CoV-2 sVNT test was performed in the same manner as in Example 5-1 on days 7 and 21.

As a result, as shown in FIG. 6B, it was confirmed that when the freeze-dried exosomes stored at 4° C. for 7 days were administered at a concentration of 0.1 μg, 0.5 μg, and 1 μg, an inhibitory effect was observed from day 7 by the administration of 1 μg of the exosomes, and an inhibitory effect close to approximately 50% was observed on day 21 when the exosomes were administered at a concentration of 0.5 μg or more on day 21. Also, as shown in FIG. 6C, it was confirmed that when the freeze-dried exosomes stored at room temperature for 7 days were administered at a concentration of 1 μg, an inhibitory effect was observed from day 7, and an inhibitory effect close to approximately 50% was observed on day 21. These results showed that the antibody production effect was similar through similar inhibitory efficiency under the same conditions when compared to the exosomes (fresh) that were not freeze-dried and stored for 7 days. Therefore, it can be seen that the effectiveness of the exosomes according to the present invention were maintained even when the exosomes according to the present invention were stored under the above-described conditions.

The above description of the present invention is for illustrative purposes, and it should be understood by those skilled in the art to which the present invention pertains that various changes and modifications can be made without departing from the technical spirit and scope of the present invention. Therefore, it should be understood that the aforementioned embodiments are intended to be illustrative in all respects and not limiting.

The invention claimed is:

1. An extracellular vesicle comprising a coronavirus-derived antigen protein or a gene encoding the protein, wherein the antigen protein is selected from the group consisting of a spike protein or a fragment thereof, a nucleocapsid protein or a fragment thereof, a membrane protein or a fragment thereof, and an envelope protein or a fragment thereof, and wherein the antigen protein or the gene encoding the protein are exogenous and loaded into the extracellular vesicle.

2. The extracellular vesicle of claim 1, wherein the coronavirus is severe acute respiratory syndrome-coronavirus-2 (SARS-CoV-2).

3. The extracellular vesicle of claim 1, wherein the antigen protein is a receptor binding domain (RBD) protein of a coronavirus-derived spike protein.

4. The extracellular vesicle of claim 1, wherein the extracellular vesicle is derived from one or more selected from the group consisting of animal cells, plant cells, or microorganisms.

5. The extracellular vesicle of claim 4, wherein the animal cells comprise one or more cells selected from the group consisting of somatic cells, germ cells, immune cells, neurons, and tumor cells.

6. The extracellular vesicle of claim 1, wherein the extracellular vesicle is derived from activated immune cells.

7. The extracellular vesicle of claim 1, wherein the extracellular vesicle expresses one or more selected from the group consisting of CD63, CD81, and Flotillin 1.

8. A vaccine composition for preventing or treating a coronavirus infection comprising the extracellular vesicle of claim 1.

9. The vaccine composition of claim 8, wherein the vaccine composition induces antigen-specific antibody production and a T cell-mediated immune response at the same time.

10. The vaccine composition of claim 8, wherein the vaccine composition is freeze-dried.

11. A health functional food for preventing or improving a coronavirus infection comprising the extracellular vesicle of claim 1.

12. A method of preventing or treating a coronavirus infection, the method comprising administering the extracellular vesicle of claim 1 to a subject in need thereof.

* * * * *